United States Patent
Guttag et al.

(10) Patent No.: US 11,114,204 B1
(45) Date of Patent: Sep. 7, 2021

(54) SYSTEM TO DETERMINE INPATIENT OR OUTPATIENT CARE AND INFORM DECISIONS ABOUT PATIENT CARE

(71) Applicant: Predictive Modeling, Inc., Lexington, MA (US)

(72) Inventors: John V. Guttag, Lexington, MA (US); Zeeshan H. Syed, Cupertino, CA (US)

(73) Assignee: Predictive Modeling, Inc., Lexington, MA (US)

( * ) Notice: Subject to any disclaimer, the term of this patent is extended or adjusted under 35 U.S.C. 154(b) by 279 days.

(21) Appl. No.: 14/678,349

(22) Filed: Apr. 3, 2015

Related U.S. Application Data

(60) Provisional application No. 61/975,060, filed on Apr. 4, 2014.

(51) Int. Cl.
*G16H 50/20* (2018.01)
*G16H 50/30* (2018.01)
*G16H 50/70* (2018.01)

(52) U.S. Cl.
CPC .............. *G16H 50/20* (2018.01); *G16H 50/30* (2018.01); *G16H 50/70* (2018.01)

(58) Field of Classification Search
CPC ............... G06F 19/345; G06F 19/3431; G06F 19/3443; G16H 50/20
USPC .......................................................... 705/2
See application file for complete search history.

(56) References Cited

U.S. PATENT DOCUMENTS

| | | |
|---|---|---|
| 7,191,150 B1 | 3/2007 | Shao |
| 8,417,541 B1 | 4/2013 | Kramer |
| 2003/0135128 A1 | 7/2003 | Suffin |
| 2004/0107088 A1 | 6/2004 | Budzinski |
| 2006/0173663 A1 | 8/2006 | Langheier |
| 2007/0269804 A1 | 11/2007 | Liew |
| 2009/0259550 A1 | 10/2009 | Mihelich |
| 2010/0184093 A1* | 7/2010 | Donovan ............... G06F 19/00 435/7.21 |
| 2011/0082712 A1 | 4/2011 | Eberhardt |

(Continued)

FOREIGN PATENT DOCUMENTS

WO   WO-2015157576 A1 * 10/2015 ............. G06Q 10/06

OTHER PUBLICATIONS

Rick Caruana, Algorithms and Applications for Multitask Learning (1996), 87-95, caruana@cmu.edu (Year: 1996).*

(Continued)

*Primary Examiner* — Hiep V Nguyen
(74) *Attorney, Agent, or Firm* — Morrison & Foerster LLP

(57) ABSTRACT

A computer-based system to determine whether patients should be treated as inpatients or outpatients. The invention makes personalized predictions about the risk and timing of adverse outcomes for the patient, and further assesses how this risk and timing may vary if the patients are treated as inpatients or outpatients. This information informs how patients are assigned to an appropriate therapy. The invention includes logic relevant to predicting patient risk, decoupling patient risk into components inherent to the patient as well as additions/subtractions associated with the choice of treatment, and predicting the timing of adverse outcomes given censored data. The invention can be extended to use in a broad range of other application domains (e.g., matching learners to courses either offered in-classroom or online for education).

26 Claims, 1 Drawing Sheet

(56) References Cited

U.S. PATENT DOCUMENTS

| | | | |
|---|---|---|---|
| 2012/0066217 A1 | 3/2012 | Eder | |
| 2012/0095943 A1 | 4/2012 | Yankov | |
| 2012/0109683 A1 | 5/2012 | Ebadollahi | |
| 2013/0022953 A1 | 1/2013 | Van Der Linden | |
| 2013/0096948 A1 | 4/2013 | Parkinson | |
| 2013/0185096 A1* | 7/2013 | Giusti | G06Q 50/24 705/3 |
| 2013/0197925 A1 | 8/2013 | Blue | |
| 2014/0058755 A1* | 2/2014 | Macoviak | G06F 19/328 705/3 |
| 2014/0108034 A1 | 4/2014 | Akbay | |
| 2014/0200824 A1 | 7/2014 | Pancoska | |
| 2015/0161331 A1 | 6/2015 | Oleynik | |
| 2015/0278470 A1 | 10/2015 | Bakker | |
| 2015/0289795 A1 | 10/2015 | Gomez | |
| 2015/0294075 A1 | 10/2015 | Rinaldo | |
| 2015/0317449 A1 | 11/2015 | Eder | |
| 2017/0083682 A1 | 3/2017 | Mcnutt | |
| 2017/0124269 A1 | 5/2017 | Mcnair | |

OTHER PUBLICATIONS

Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).

Final Office Action dated Dec. 26, 2018, for U.S. Appl. No. 14/809,528, filed Jul. 27, 2015, 30 pages.

Final Office Action dated Jan. 7, 2019, for U.S. Appl. No. 14/736,470, filed Jun. 11, 2015, fifteen pages.

Final Office Action dated Jul. 23, 2018, for U.S. Appl. No. 14/622,112, filed Feb. 13, 2015, eleven pages.

Non-Final Office Action dated Feb. 26, 2018, for U.S. Appl. No. 14/736,470, filed Jun. 11, 2015, sixteen pages.

Non-Final Office Action dated Jan. 29, 2020, for U.S. Appl. No. 14/809,528, filed Jul. 27, 2015, 20 pages.

Non-Final Office Action dated Mar. 14, 2019, for U.S. Appl. No. 14/622,112, filed Feb. 13, 2015, ten pages.

Non-Final Office Action dated Mar. 27, 2020, for U.S. Appl. No. 14/622,112, filed Feb. 13, 2015, nine pages.

Non-Final Office Action dated Mar. 9, 2020, for U.S. Appl. No. 14/736,470, filed Jun. 11, 2015, nine pages.

Non-Final Office Action dated May 1, 2018, for U.S. Appl. No. 14/809,528, filed Jul. 27, 2015, 25 pages.

Non-Finai Office Action dated Sep. 28, 2017, for U.S. Appl. No. 14/622,112, filed Feb. 13, 2015, fifteen pages.

Final Office Action dated Jul. 21, 2020, for U.S. Appl. No. 14/809,528, filed Jul. 27, 2015, twenty pages.

Final Office Action dated Nov. 16, 2020, for U.S. Appl. No. 14/736,470, filed Jun. 11, 2015, eleven pages.

Caruana, Rich. (1997). "Multitask Learning," Kluwer Academic Publishers, Manufactured in the Netherlands, Machine Learning, 35 pages.

Caruana, Rich. (May 1996). "Algorithms and Applications for Multitask Learning," School of Computer Science, Carnegie Mellon University, Pittsburgh, PA, 9 pages.

Final Office Action dated Dec. 21, 2020, for U.S. Appl. No. 14/622,112, filed Feb. 13, 2015, nine pages.

\* cited by examiner

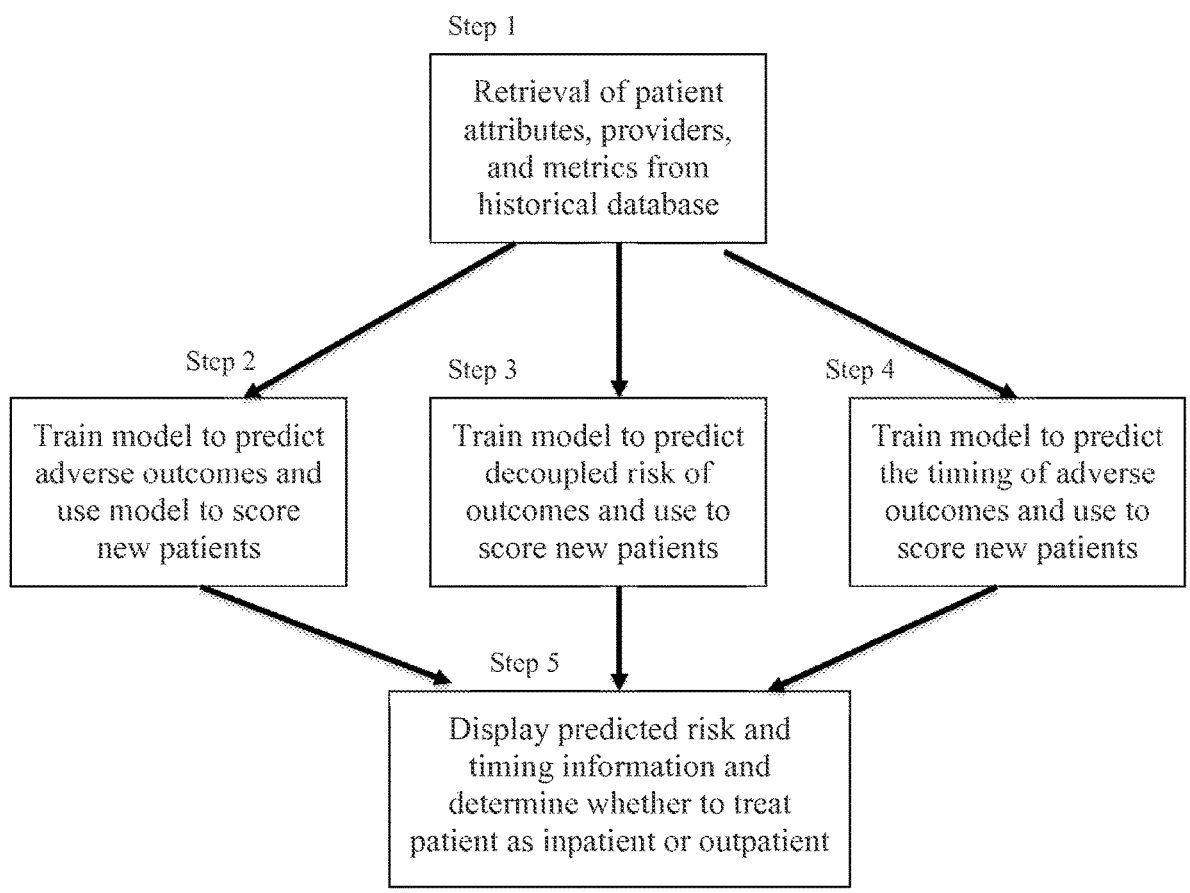

SYSTEM TO DETERMINE INPATIENT OR OUTPATIENT CARE AND INFORM DECISIONS ABOUT PATIENT CARE

RELATED APPLICATIONS

This application claims priority to U.S. Provisional Application 61/975,060 filed Apr. 4, 2014, the entirety of which is herein incorporated by reference.

FIELD OF THE INVENTION

The present invention comprises a computer system to objectively determine which patients should be treated by providers as inpatients or outpatients.

DESCRIPTION OF THE RELATED ART

The decision to treat a patient as an inpatient or outpatient significantly impacts patients, providers, and payors. From the perspective of quality and outcomes, there is a downside to treating high-risk patients as outpatients, since post-discharge complications put patients at increased risk. On the other hand, keeping low-risk patients in the hospital as inpatients potentially exposes them to hospital acquired-complications (e.g., nosocomial infections) and incurs additional costs. The decision to treat a patient as an outpatient vs. inpatient, and the associated variation in the amount of time spent in the hospital, also has a bearing on patient satisfaction—with patients often preferring shorter stays that allow them to get back to their daily routine quickly. Finally, there is a substantial effect of the decision to treat patients as inpatients vs. outpatients on costs, reimbursements, and finances. For example, Medicare beneficiaries treated by hospitals as outpatients are not covered by Medicare Part A. Instead, the stay is considered a Part B expense and results in lower reimbursements (affecting both providers and payors) and higher co-pays and co-insurance costs (affecting patients).

The challenge in this setting is how to make the determination of whether a patient should be treated as an inpatient or an outpatient. Existing art is focused on requiring clinicians to use their individual judgment and evaluation to make the determination. This is a largely ad hoc and non-reproducible process. The weakness of this approach is evidenced by the frequency of audits of inpatient admissions as being "medically necessary" or "medically unnecessary." In contrast to this, there are also frequent lawsuits to hospitals when patients are believed to have been incorrectly treated in an outpatient setting and may have benefited from inpatient admission.

One of the key challenges is that the interests of patients, providers, and payors are often misaligned. Patients and providers typically benefit financially from having their stay in a hospital treated as inpatient. For providers, this is because reimbursements for inpatient care are higher than reimbursements for outpatient care. For patients, this is because outpatient care is associated with substantial co-pays and co-insurance, unlike inpatient care. In contrast to this, payors are incentivized from a cost-cutting perspective to reduce the number of patients treated on an inpatient basis (because they have to cover the costs deferred from providers and patients when patients are treated as inpatients). As a result, there are often diverging views on inpatient admissions being necessary or unnecessary. Providers are audited for their choices to admit patients as inpatients, and there are an increasing number of penalties (e.g., on readmissions) designed to discourage hospitals from inpatient admissions.

In this setting, it would be beneficial to have an objective tool for determining whether a patient should be treated as an impatient or as an outpatient. Notably, with the "two midnight" ruling from CMS expected to fully come into practice within the next few months, providers will be reimbursed for inpatient care if a patient is admitted to the hospital for two midnights and providers can justify inpatient admission for the case to qualify for Medicare Part A reimbursement. Both patients and providers may not know for sure, until they submit the bill to Medicare, whether stays will be approved as inpatient care due to the subjective determination of inpatient status being "medically necessary." While providers have the opportunity to resubmit claims under Part B, for patients this may be an unwelcome development as the provider may also seek from them co-payments allowed under Part B. There is therefore a growing need for tools that can objectively determine whether a patient should be treated as inpatient vs. outpatient—and to do so using data that are available early on during a patient encounter so as to avoid status changes subsequently.

Such tools for inpatient vs. outpatient determination have value in three different settings: (1) objectively and reproducibly resolving the question of admissions being "medically necessary" or "medically unnecessary" for reimbursement purposes; (2) providing a means whereby patients have some degree of confidence about their co-pays and co-insurances early on during the course of their stay and can make informed decisions about care; and (3) helping identify patients at high risk who are inappropriately treated as outpatients and may in fact benefit substantially from inpatient treatment.

SUMMARY OF THE INVENTION

The present invention comprises a computer system that can objectively and reproducibly determine whether patients should be treated as inpatients vs. outpatients.

The invention uses sophisticated machine learning to construct models that can predict the risk of adverse outcomes (e.g., mortality, different morbidity events, and decisions by the Medicare panel). These models are constructed using historical case records available through either individual repositories or linked data repositories. The model training process focuses on learning a mapping between data that are commonly collected during early stages of patient encounters (e.g., patient demographics, history and physical exam findings, comorbidities, diagnoses, procedures, lab findings, clinical risk scores, inpatient/outpatient status, etc.) and either adverse outcomes reported subsequently during these patient encounters or decisions from Medicare panels. The invention proposes use of the predictions generated by these models derived from sophisticated machine learning as they are applied to new patients to inform judgment as to whether these new patients should be considered candidates for inpatient admission or outpatient treatment.

To address the issue that historical data may be affected by previously-made subjective decisions about whether to treat patients as inpatients or outpatients, the invention additionally includes a component to decouple patient risk into (i) risk that is inherent to the patient, and (ii) risk that is inherent to the choice of treatment setting. For example, if a historical case record shows that an inpatient does not experience an adverse outcome, it may be incorrect to assume that the patient was low risk and should therefore have been treated as an outpatient. While this is certainly possible, it may also be the case that the risk of adverse outcomes was reduced by the process of inpatient admission and the absence of adverse outcomes may reflect that the correct decision was made. The invention proposes a solution to such issues and seeks to decompose patient risk inferred from historical data into a baseline estimate that is not correlated with the past decision to treat a patient as inpatient or outpatient (i.e., the inherent risk unrelated to choice of treatment), as well as incremental additions or subtractions to this risk associated with subjective decisions in the past to treat patients as inpatients or outpatients (i.e., the variable risk to the patient associated with inpatient or outpatient treatment). This ability of the invention to decompose patient risk in this manner provides for more meaningful decisions to be made about inpatient vs. outpatient treatment, that potentially consider not only the patient's baseline risk but also how it may be modified by inpatient or outpatient therapy.

The invention finally also comprises a component to predict the timing of events as they may be expected to occur during the course of a patient's encounter. This adds utility beyond simply predicting whether an adverse outcome may or may not occur by providing a sense for when such events may be reasonably believed to occur during a patient's evolution. The time-frame for adverse outcomes may also have bearing upon whether to manage potential events during an inpatient admission or through rigorous monitoring and therapy in an outpatient setting. To achieve this, the invention provides a module to train models to predict the timing of events using as input censored clinical data. This module can then be used to assess the time-frame over which adverse outcomes may occur. In addition to dealing with time-varying data (e.g., survival or mortality data), it also comprises a component to handle censoring (i.e., labels are only partially known as may be the case if patients drop out of a study). The focus on being able to handle censored and survival data as necessary follows from the realization that clinical data generally occurs in such a form. The invention therefore proposes use of robust methods that are able to build predictive models in the setting of such data for assessing patient risk.

We note that while the invention is proposed here in terms of exploiting opportunities to improve the logistics of clinical care, it may have value in other domains of medicine (e.g., more generally comparing between treatment arms) as well as in non-medical disciplines, e.g., education (where students can be matched to learning modules that are delivered either in an online manner or an in-classroom manner with students dropping out of the modules and quantities such as the time taken to learn concepts being interesting).

BRIEF DESCRIPTION OF THE DRAWINGS

FIG. 1 illustrates a flow diagram of the system to determine whether patients should be treated as inpatient vs. outpatient.

DETAILED DESCRIPTION

FIG. 1 illustrates a flow diagram of the invention. The steps shown are described below in more detail.

STEP 1: We start out with historical case records in a database. We associate with each case previously treated in either an inpatient or outpatient setting a plurality of attributes based on but not limited to the patient's demographics (e.g., age, gender); history (e.g., prior myocardial infarction) and physical exam findings (e.g., edema around the ankles); comorbidities (e.g., hypertension); laboratory reports (e.g., high troponin levels; low ejection fraction); admission type (e.g., transfer from another hospital, elective admission); and insurance (e.g., Medicare). We denote such a vector of case attributes associated with each patient as $x_i$ where i=1 ... N for a total of N patients in the database and $x_i(j)$ is the value of the j-th attribute for case i out of a total of d possible attributes. We also associate with each case a scalar indicator $s_i \in \{0,1\}$ that indicates whether patient i was treated in an inpatient ("1") or outpatient ("0") setting. We further associate with each case i a vector $y_i$ comprising whether different outcomes (e.g., different mortality and morbidity endpoints) did or did not occur, a vector $t_i$ comprising the times after patient presentation when these respective outcomes occurred (or a token such as "NA" if these outcomes did not take place), and a scalar $m_1$ indicating the maximum time that the patient was followed-up. Consistent with the notation used for case attributes above, $y_i(j) \in \{-1,+1\}$ corresponds to the indicator about whether the j-th outcome of interest for patient i occurred ("+1") or not ("−1"). Similarly, $t_i(j)$ denotes the time after patient presentation when the j-th outcome of interest for case i occurred (or a token indicating that the event did not take place).

STEP 2: For each outcome we train models to predict the risk of clinical events. In one embodiment, model training for a given outcome is achieved through support vector machine (SVM) classification and is supplemented with Platt scaling to obtain probabilistic estimates.

More formally, for an outcome j we train a model to predict this outcome on the basis of information in the attributes of the presenting case by solving:

$$\min_{w,\xi} \frac{1}{2}\|w\|^2 + C\sum_{i=1}^{N} \xi_i$$

$$\text{s.t.} \quad y_i(j)(wx_i) \geq 1 - \xi_i \quad \forall i = 1, \ldots, N$$

$$\xi_i \geq 0 \forall i = 1, \ldots, N$$

where w is the vector of model coefficients and the $\xi_i$ terms represent slack variables. The cost parameter C can be chosen by experimenting with different values through cross-validation and reflects the extent to which errors during the training process are weighted relative to increases in the complexity of the model. The weight vector w above can be used to subsequently predict whether a new case will experience a given outcome or not by assigning the case a +1 or −1 label based on the sign of the dot product between the weight vector w and the attributes x for the case (i.e., the predicted label for the new case corresponds to sign(wx)).

To obtain more fine-grained information (i.e., beyond a +1 or −1 predicted labeling of the patients) a probabilistic estimate for the outcome can be obtained using a Platt scaling function to further transform the dot product wx as follows:

$$f(wx) = \frac{1}{1 + \exp(A(wx) + B)}$$

where A and B are obtained on data held out from the model training process above by solving:

$$-\sum_{i=1}^{N}(z_i\log(p_i) + (1-z_i)\log(1-p_i))$$

with:

$$p_i = \frac{1}{1+\exp(A(wx_i)+B)}$$

$$z_i = \begin{cases} \frac{N_+ + 1}{N_- + 2} & \text{if } y_i(j) = +1 \\ \frac{1}{N_- + 2} & \text{if } y_i(j) = -1 \end{cases}$$

In the notation above, $N_+$ denotes the number of positive examples in the data used for model calibration, and $N_-$ denotes the number of negative examples. The Platt scaling function derived in this manner can be used along with the weight vector w to subsequently assign a probabilistic score for a given outcome to a new patient (i.e., the predicted probability corresponds to f(wx)).

In extensions of this embodiment, the training process above may be carried out using cost-sensitive weighting to account for imbalance between positive and negative examples. The training process may also use kernels (e.g., polynomial, radial basis function) to account for non-linear decision boundaries. In other embodiments, model training may be achieved through the use of supervised learning methods (e.g., logistic regression, decision trees, random forests, neural nets, nearest neighbors etc.) or unsupervised learning methods (e.g., 1-class SVM, nearest neighbor-based anomaly detection, clustering-based anomaly detection etc.) or 1.5 class learning methods (e.g., ½ learning, 1+ learning, 1-to-2 and 2-to-1 learning, 1-with-2 learning etc.) or semi-supervised learning. In further embodiments, the model training may also be achieved through the use of learning algorithms designed for multivariate error functions (e.g., AUROC-maximizing SVM, recall-maximizing SVM, precision-maximizing SVM, F1-maximizing SVRM), or where models are trained for the different outcomes jointly (e.g., multi-task learning), or where the models are transferred between outcomes (e.g., transfer learning). The supplementary processing of model outputs to obtain probabilistic estimates—for use with models that do not directly produce probabilistic estimates or to better calibrate models that do produce probabilistic estimates—can be achieved in these embodiments through further use of isotonic regression, binning, or adaptive calibration (i.e., as alternate methodologies beyond Platt scaling).

In further embodiments, in addition to creating a model to predict the risk of an adverse clinical outcome using data from both historical inpatient and outpatient cases pooled together, the invention uses data from either inpatients or outpatients alone to guide how patients should be treated.

In still other embodiments, in addition to using data within a single registry the invention also uses data across registries or datasets (e.g., relate patients in registry A with outcomes from the national death registry for the purpose of modeling).

In a final embodiment, the invention can further customize the models obtained through the plurality of approaches described here for individual providers, i.e., predict the risk of adverse outcomes given that treatment will delivered in an inpatient or an outpatient by a specific provider. This can be achieved through the use of transfer learning or multi-task learning to obtain a provider-specific estimate of the risk of adverse outcomes during inpatient or outpatient treatment.

STEP 3: To decouple patient risk into a component explained by patient presentation and a component explained by the decision to admit the patient as inpatient or outpatient, the invention makes use of multi-task learning. In one embodiment, the invention uses a task-coupling parameter formulation where the prediction of patient risk in an inpatient setting and outpatient setting for a given outcome j are treated as related tasks. Using the notation that r $\in \{0,1\}$ corresponds to the related tasks, with r=0 representing the task of predicting patient risk in an outpatient setting and r=1 representing the task of predicting patient risk in an inpatient setting, the model weight vectors to be learned for both predicting inpatient and outpatient risk can be represented as:

$$w_0 = w_* + v_0$$

$$w_1 = w_* + v_1$$

where $w_*$ is the component of the model weight vectors that is common to both the task of predicting inpatient and outpatient risk (and can be interpreted as the component of risk inherent to the patient's presentation and unrelated to the choice of inpatient or outpatient treatment), and $v_0$ and $v_1$ are the components of the model weight vectors that are specific to the tasks of predicting outpatient or inpatient risk (and can be interpreted as producing the incremental additions of subtractions on top of the patient's inherent risk due to choice of treatment).

$$\min_{w_*, v_r, \xi_{ir}} \sum_{r=0}^{1} \sum_{i=1}^{N} \xi_{ir} + \lambda \sum_{r=0}^{1} \|v_r\|^2 + \gamma \|w_*\|^2$$

$$\text{s.t.} \quad y_i(j)(w_* + v_0)x_i \geq 1 - \xi_{i0} \quad \forall i \mid s_i = 0$$
$$y_i(j)(w_* + v_1)x_i \geq 1 - \xi_{i1} \quad \forall i \mid s_i = 1$$
$$\xi_{ir} \geq 0 \quad \forall r = 0, 1$$

where the $\xi_{ir}$ represent slack variables as before and the $\lambda$ and $\gamma$ terms represent positive regularization parameters that are chosen by cross-validation. To address the issue of imbalance between inpatient and outpatient cases available for training, the above formulation may be further generalized as follows with different regularization factors $\rho$, $\lambda$, and $\gamma$ assigned to the weights and slack variables:

$$\min_{w_*, v_r, \xi_{ir}} \sum_{r=0}^{1} \rho_r \sum_{i=1}^{N} \xi_{ir} + \lambda_0 \|v_0\|^2 + \lambda_1 \|v_1\|^2 + \gamma \|w_*\|^2$$

$$\text{s.t.} \quad y_i(j)(w_* + v_0)x_i \geq 1 - \xi_{i0} \quad \forall i \mid s_i = 0$$
$$y_i(j)(w_* + v_1)x_i \geq 1 - \xi_{i1} \quad \forall i \mid s_i = 1$$
$$\xi_{ir} \geq 0 \quad \forall r = 0, 1$$

The weight vectors $w_*$, $v_0$ and $v_1$ resulting from this training of models using task coupling can be subsequently used to assess new patients in terms of their inherent risk (using $w_*$), the incremental risk associated with outpatient care (using $v_0$), the incremental risk associated with inpatient care (using $v_1$), the total risk associated with outpatient care (using both $w_*$ and $v_0$), and the total risk associated with inpatient care (using both $w_*$ and $v_1$) to inform decision making about whether to admit patients as inpatients or outpatients.

Consistent with the discussion above, we can use Platt scaling to obtain probabilistic information about inherent patient risk and the incremental changes in risk associated with inpatient or outpatient treatment. Specifically, without loss of generality considering the outpatient case, the overall probabilistic risk score assigned to a patient for a given outcome when treated as an outpatient is $f((w_*+v_0)x)$ while the inherent risk for the patient is $f((w_*)x)$. The incremental increase or decrease in risk can be found as the difference between these quantities. The approach for inpatient treatment can be carried out in an identical manner using $v_1$ instead of $v_0$.

In further embodiments, the decoupling of patient risk can be achieved through the use of other multi-task learning formulations (i.e., beyond task parameter coupling), co-training, transfer learning, priors, shrinkage, hierarchical modeling, or by separately training models using inpatient or outpatient data only. In other embodiments, the probabilistic calibration process can also be performed using multiple Platt scaling functions using parameters A and B that are either shared between the inpatient and outpatient tasks or selectively varied between the two.

In still other embodiments, consistent with the discussion for Step 2, the base approach used for modeling can be changed from SVM classification to one of a plurality of other approaches (e.g., neural nets, nearest neighbors, decision trees, etc.) as described for Step 2 and the base approach for probabilistic calibration can be changed from Platt scaling to one of a plurality of other approaches (e.g., isotonic regression, binning, etc.) as also described for Step 2.

In other variations, the decoupling of patient risk can also be achieved through propensity-based matching, where a model trained on an inpatient/outpatient mix is used to identify similar groups of patients, and the risk of patients within this similar group treated as inpatients is compared to the risk of these patients within this similar group treated as outpatients.

In still other embodiments, the modeling described here can be carried out on either individual registries or databases, or through multiple registries or databases linked together.

In a final embodiment, consistent with Step 2, the invention can further customize the models obtained through the plurality of approaches described here for individual providers through use of transfer learning or multi-task learning to obtain provider-specific decoupled risk estimates.

STEP 4: To predict the timing of a given outcome for patients, in one embodiment we use an SVM approach for censored targets. Specifically, for a given outcome j we associated with each patient i the tuple $(x_i, l_i, u_i)$ where $x_i$ denotes attributes of the case as before and for patients who experience the outcome (i.e., $y_i(j)=+1$):

$$l_i = u_i = t_i$$

while for patients who do not experience the outcome (i.e., $y_i(j)=-1$):

$$l_i = m_i$$

$$u_i = +\infty$$

Using this notation, we learn a weight vector to predict the timing of a given outcome by solving:

$$\min_{w,\xi_i,\xi_i^*} \frac{1}{2}\|w\|^2 + C\left(\sum_{i \in U} \xi_i + \sum_{i \in L} \xi_i^*\right)$$

$$\text{s.t.} \quad (wx_i) - u_i \leq \xi_i \quad \forall i \in U$$
$$l_i - (wx_i) \leq \xi_i^* \quad \forall i \in L$$
$$\xi_i \geq 0 \quad \forall i \in U$$
$$\xi_i^* \geq 0 \quad \forall i \in L$$

where the set U comprises all cases where an event took place (i.e., $y_i(j)=+1$) and the set L comprises all cases (i.e., $y_i(j)=+1$ or $-1$).

In another embodiment, we use an alternate SVM formulation for censored targets that searches for a function of the covariates such that the resulting values are as concordant as possible with the observed events. Specifically, for a given outcome j we associated with each patient i the tuple $(x_i, v_i, \delta_i)$ where $x_i$ denotes attributes of the case as before, $v_i$ is set to $t_i$ if $y_i(j)=+1$ or $m_i$ if $y_i(j)=-1$, and $\delta_i$ is set to 1 if $y_i(j)=+1$ or 0 if $y_i(j)=-1$. The different patients are also sorted according to the outcome or censoring time so that $v_i \geq v_{i-1}$. Using this notation and sorted representation, we learn a weight vector to predict the timing of a given outcome by solving:

$$\min_{w,\varsigma_{i,i-1},\xi_i,\xi_i^*} \frac{1}{2}\|w^2\| + \gamma \sum_{i=2}^{N} \varsigma_{i,i-1} + \lambda \sum_{i=2}^{N}(\xi_i + \xi_i^*)$$

$$\text{s.t.} \quad wx_i - wx_{i-1} + \varsigma_{i,i-1} \geq v_i - v_{i-1} \quad \forall i = 2, \ldots, N$$
$$wx_i + \xi_i \geq v_i \quad \forall i = 1, \ldots, N$$
$$-\delta_i wx_i + \xi_i^* \geq -\delta_i v_i \quad \forall i = 1, \ldots, N$$
$$\varsigma_{i,i-1} \geq 0 \quad \forall i = 2, \ldots, N$$
$$\xi_i \geq 0 \quad \forall i = 1, \ldots, N$$
$$\xi_i^* \geq 0 \quad \forall i = 1, \ldots, N$$

where $\lambda$ and $\gamma$ represent regularization parameters chosen by cross-validation and $\varsigma_{i,i-1}$, $\xi_i$ and $\xi_i^*$ represent slack variables.

In still other embodiments, the timing of events is predicted by support vector regression, linear regression, non-linear regression, multivariate regression, robust regression, neural network regression, random forest regression, nearest neighbors, and proportional hazards regression.

In further embodiments, timing information can be reduced to a finite number of discrete values (e.g., predict whether adverse outcomes occur within days 1-3, days 4-7, days 8-10, etc.) and solved for using multi-class classification approaches such as multi-class SVMs, neural nets, decision trees, random forests, and nearest neighbors. In yet more embodiments, the invention can supplement a prediction about the timing of events with a probability distribution using the plurality of methods just described over the different time points when outcomes may occur.

In still more embodiments, the modeling described here can be carried out on either inpatient or outpatient databases, or a combination of both; and also on either individual registries or databases, or through multiple registries or databases linked together.

In a final embodiment, consistent with steps 2 and 3, the invention can further customize the models obtained through the plurality of approaches described here for individual providers through use of transfer learning or multi-task learning to obtain provider-specific estimates of the timings of adverse outcomes during inpatient or outpatient treatment.

STEP 5: The determination of whether to treat a patient as inpatient or outpatient can be made on the basis of the information obtained through Steps 2-4. In one embodiment, this decision is made at the discretion of the physician with the invention providing textual and graphical outputs indicating the risk to the patient (both with and without the separation into the various decoupled components described earlier) and the time at which adverse outcomes are most likely to occur. In another embodiment, this decision is made in an automated or semi-automated manner based on rules and thresholds defined on risk and timing predictions for adverse outcomes. In a further embodiment, this decision can also be made in an automated or semi-automated manner based on a determination of whether patient outcomes will be improved based on risk predictions made about the patient being treated in an inpatient or outpatient setting or whether an outcome is imminent based on timing predictions made about the patient being treated in an inpatient or outpatient setting. In other embodiments, the invention also focuses on presenting information to patients or payors, thereby allowing them to participate in the admission decision-making process.

In different embodiments, the invention can visually display data to caregivers using software installed on a computer, through a web-based interface, or as applications running on a smartphone or tablet. In other variations, the invention can also log the results to a database and populate decisions that were made, as well as predictions and observed outcomes. In a final embodiment, the information about predicted patient risk and timing of adverse outcomes can also be used to generate filled-in forms and other workflow materials that can be used to supplement notes about decisions to treat patients as inpatients or outpatients that are submitted to regulatory agencies and payors (e.g., CMS) to support the decisions that are made (e.g., to justify admissions for the "two midnight rule").

The following is claimed:

1. A method of determining whether to treat a patient as an inpatient or an outpatient, comprising the steps of:
    creating a set of training data comprising case attributes and outcomes for each patient of a plurality of patients who was treated as an inpatient or an outpatient;
    training a plurality of models simultaneously via multi-task learning based on the set of training data;
    obtaining, via an input device, a set of attributes associated with a new patient;
    obtaining, by a one or more processors, the plurality of trained models to calculate inpatient risk and outpatient risk, decoupled from inherent patient risk resulting from potential courses of treatment,
        wherein the plurality of trained models comprises: a first weight vector for predicting an inherent risk of a future outcome, a second weight vector for predicting an inpatient risk of the future outcome, and a third weight vector for predicting an outpatient risk of the future outcome;
    applying, by the one or more processors, the plurality of trained models to assess the new patient who is a candidate for inpatient or outpatient treatment to predict decoupled inpatient and outpatient risks of outcomes of potential courses of treatment for that new patient by:
        providing the set of attributes associated with the new patient to the plurality of trained models;
        determining, by the one or more processors, an inherent risk of the future outcome to the new patient based on the first weight vector and the set of attributes associated with the new patient;
        determining, by the one or more processors, an inpatient risk of the future outcome relative to the inherent risk to the new patient based on the second weight vector and the set of attributes associated with the new patient;
        determining an outpatient risk of the future outcome relative to the inherent risk to the new patient based on the third weight vector and the set of attributes associated with the new patient;
        calculating a first total risk value associated with inpatient care based on the determined inherent risk of the future outcome and the inpatient risk of the future outcome;
        calculating a second total risk value associated with outpatient care based on the determined inherent risk of the future outcome and the outpatient risk of the future outcome; and
    providing textual or graphical outputs indicating the inherent risk of the future outcome to the new patient, the inpatient risk of the future outcome to the new patient, the outpatient risk of the future outcome to the new patient, the first total risk to the new patient, the second total risk to the new patient, or a combination thereof;
    automatically determining whether the new patient is to be treated as an inpatient or outpatient based on a set of rules and thresholds, wherein the set of rules and thresholds includes the inherent risk of the future outcome, the inpatient risk of the future outcome, the outpatient risk of the future outcome, or a combination thereof.

2. The method as recited in claim 1, further comprising a use of supervised learning, unsupervised learning, 1.5 class learning, semisupervised learning, multi-task learning and transfer learning, or a variation thereof.

3. The method as recited in claim 1, further comprising customizing the plurality of models for individual providers or groups of providers.

4. The method as recited in claim 1, further comprising a use of probabilistic calibration where parameters are either shared between inpatient and outpatient tasks or selectively varied between the two.

5. The method as recited in claim 1, further comprising a use of propensity-based matching and a comparison of risk differences between propensity-matched patients who are treated as inpatients or outpatients.

6. The method as recited in claim 1, wherein the plurality of models are trained by measuring timing of outcomes for patients.

7. The method as recited in claim 6, further comprising a use of support vector machine formulations for censored targets, support vector regression, linear regression, non-linear regression, multivariate regression, robust regression, neural network regression, random forest regression, nearest neighbors, or proportional hazards regression.

8. The method as recited in claim 6, further comprising a reduction of timing information to a finite number of discrete values and a use of multi-class classification.

9. The method as recited in claim 6, further comprising a prediction of a probability distribution over potential timing of events.

10. The method as recited in claim 1, further comprising comparing how patient outcomes will be changed between inpatient or outpatient care.

11. The method as recited in claim 10, wherein comparing how patient outcomes will be changed between inpatient or outpatient care is achieved in an automated or semi-automated manner based on the set of rules and thresholds.

12. The method as recited in claim 10, wherein comparing how patient outcomes will be changed between inpatient or outpatient care is achieved based on imminence of adverse outcomes.

13. A computer-based system to determine whether to treat a patient as an inpatient or an outpatient:
one or more processors;
a memory; and
one or more programs, wherein the one or more programs are stored in the memory and configured to be executed by the one or more processors, the one or more programs including instructions for:
creating a set of training data comprising case attributes and outcomes for each patient of a plurality of patients who was treated as an inpatient or an outpatient;
training a plurality of models simultaneously via multi-task learning based on the set of training data;
obtaining, via an input device, a set of attributes associated with a new patient;
obtaining, by the one or more processors, the plurality of trained models to calculate inpatient risk and outpatient risk decoupled from inherent patient risk resulting from potential courses of treatment,
wherein the plurality of trained models comprises: a first weight vector for predicting an inherent risk of a future outcome, a second weight vector for predicting an inpatient risk of the future outcome, and a third weight vector for predicting an outpatient risk of the future outcome;
applying, by the one or more processors, the plurality of trained models to assess the new patient who is a candidate for inpatient or outpatient treatment to predict decoupled inpatient and outpatient risks of outcomes from potential courses of treatment for that new patient by:
providing the set of attributes associated with the new patient to the plurality of trained models;
determining, by the one or more processors, an inherent risk of the future outcome to the new patient based on the first weight vector and the set of attributes associated with the new patient;
determining, by the one or more processors, an inpatient risk of the future outcome relative to the inherent risk to the new patient based on the second weight vector and the set of attributes associated with the new patient;
determining an outpatient risk of the future outcome relative to the inherent risk to the new patient based on the third weight vector and the set of attributes associated with the new patient;
calculating a first total risk value associated with inpatient care based on the determined inherent risk of the future outcome and the inpatient risk of the future outcome;
calculating a second total risk value associated with outpatient care based on the determined inherent risk of the future outcome and the outpatient risk of the future outcome; and providing textual or graphical outputs indicating the inherent risk of the future outcome, the inpatient risk of the future outcome, the outpatient risk of the future outcome, the first total risk, the second total risk, or a combination thereof;
automatically determining whether the new patient is to be treated as an inpatient or outpatient based on a set of rules and thresholds, wherein the set of rules and thresholds includes the inherent risk of the future outcome, the inpatient risk of the future outcome, the outpatient risk of the future outcome, or a combination thereof.

14. The computer-based system as recited in claim 13, further comprising a use of supervised learning, unsupervised learning, 1.5 class learning, semi-supervised learning, multi-task learning or transfer learning, or a variation thereof.

15. The computer-based system as recited in claim 13, further comprising customizing the plurality of models for individual providers or groups of providers.

16. The computer-based system as recited in claim 13, further comprising a use of probabilistic calibration where parameters are either shared between inpatient and outpatient tasks or selectively varied between the two.

17. The computer-based system as recited in claim 13, further comprising a use of propensity-based matching and a comparison of risk differences between propensity matched patients who are treated as inpatients or outpatients.

18. The computer-based system as recited in claim 13, wherein the plurality of models are trained by measuring timing of outcomes for patients.

19. The computer-based system as recited in claim 18, further comprising a use of SVM formulations for censored targets.

20. The computer-based system as recited in claim 18, further comprising a use of support vector regression, linear regression, non-linear regression, multivariate regression, robust regression, neural network regression, random forest regression, nearest neighbors, or proportional hazards regression.

21. The computer-based system as recited in claim 18, further comprising a reduction of timing information to a finite number of discrete values and a use of multi-class classification.

22. The computer-based system as recited in claim 18, further comprising a prediction of a probability distribution over potential timing of events.

23. The computer-based system as recited in claim 13, further comprising comparing how patient outcomes will be changed between inpatient or outpatient care.

24. The computer-based system as recited in claim 13, wherein comparing how patient outcomes will be changed between inpatient or outpatient care is achieved in an automated or semi-automated manner based on the set of rules and thresholds.

25. The computer-based system as recited in claim 13, wherein comparing how patient outcomes will be changed between inpatient or outpatient care is achieved based on imminence of adverse outcomes.

26. The computer-based system as recited in claim 13, wherein results of the automatic determination are archived and used to complete forms to be submitted to payors.

* * * * *